United States Patent [19]
Summers

[11] Patent Number: 5,566,823
[45] Date of Patent: Oct. 22, 1996

[54] TOOTHBRUSH HOLDER

[76] Inventor: Shirley F. Summers, R.R. 3, Box 527, Marion, Ill. 62959

[21] Appl. No.: 376,798

[22] Filed: Jan. 22, 1995

[51] Int. Cl.$^6$ ............................................. B65D 83/10
[52] U.S. Cl. .................. 206/209.1; 206/209; 206/362.1; 206/362.2; 132/310
[58] Field of Search .............................. 206/209, 209.1, 206/210, 362, 362.1, 362.2, 370, 372, 375; 422/300; 132/308, 310

[56] References Cited

U.S. PATENT DOCUMENTS

| | | | |
|---|---|---|---|
| 1,507,466 | 9/1929 | Collins | 206/209.1 |
| 2,292,626 | 8/1942 | Ferguson | 206/210 |
| 2,608,294 | 8/1952 | Ward | 206/362.1 |
| 3,191,712 | 7/1964 | Holmes et al. | 206/362.1 X |
| 3,342,544 | 9/1967 | Wriel | 422/300 |
| 3,371,260 | 2/1968 | Jackson et al. | 206/362.1 X |
| 3,727,748 | 4/1973 | Brown | 206/362.1 |
| 3,748,094 | 7/1973 | Scheidell | 21/83 |
| 3,881,868 | 5/1975 | Duke | 21/83 |
| 3,884,635 | 5/1975 | Sloan | 206/209 X |
| 3,904,362 | 9/1975 | DiPaolo | 21/87 |
| 4,214,657 | 7/1980 | Winston | 206/209 |
| 4,473,152 | 9/1984 | Jump, Jr. et al. | 206/209.1 |
| 4,585,119 | 4/1986 | Boyington | 206/209.1 |
| 4,658,957 | 4/1987 | Guth et al. | 206/365 |
| 4,756,412 | 7/1988 | Graves et al. | 206/315.11 |
| 4,759,383 | 7/1988 | Phillips | 134/93 |
| 4,915,219 | 4/1990 | Ottimo | 206/209.1 |
| 4,978,003 | 12/1990 | Foster | 206/217 |
| 4,995,511 | 2/1991 | Evans | 206/362.1 |
| 4,997,629 | 3/1991 | Marchand et al. | 422/300 |

Primary Examiner—Paul T. Sewell
Assistant Examiner—Tara L. Laster
Attorney, Agent, or Firm—Grace J. Fishel

[57] ABSTRACT

A sanitary holder for storing toothbrushes in a tray with a plurality of separate receptacles for holding a liquid antiseptic into which a bristle end of a toothbrush is immersed. The tray is stored in a container with a cap and is slid in and out of the container with a handle attached to the tray.

8 Claims, 1 Drawing Sheet

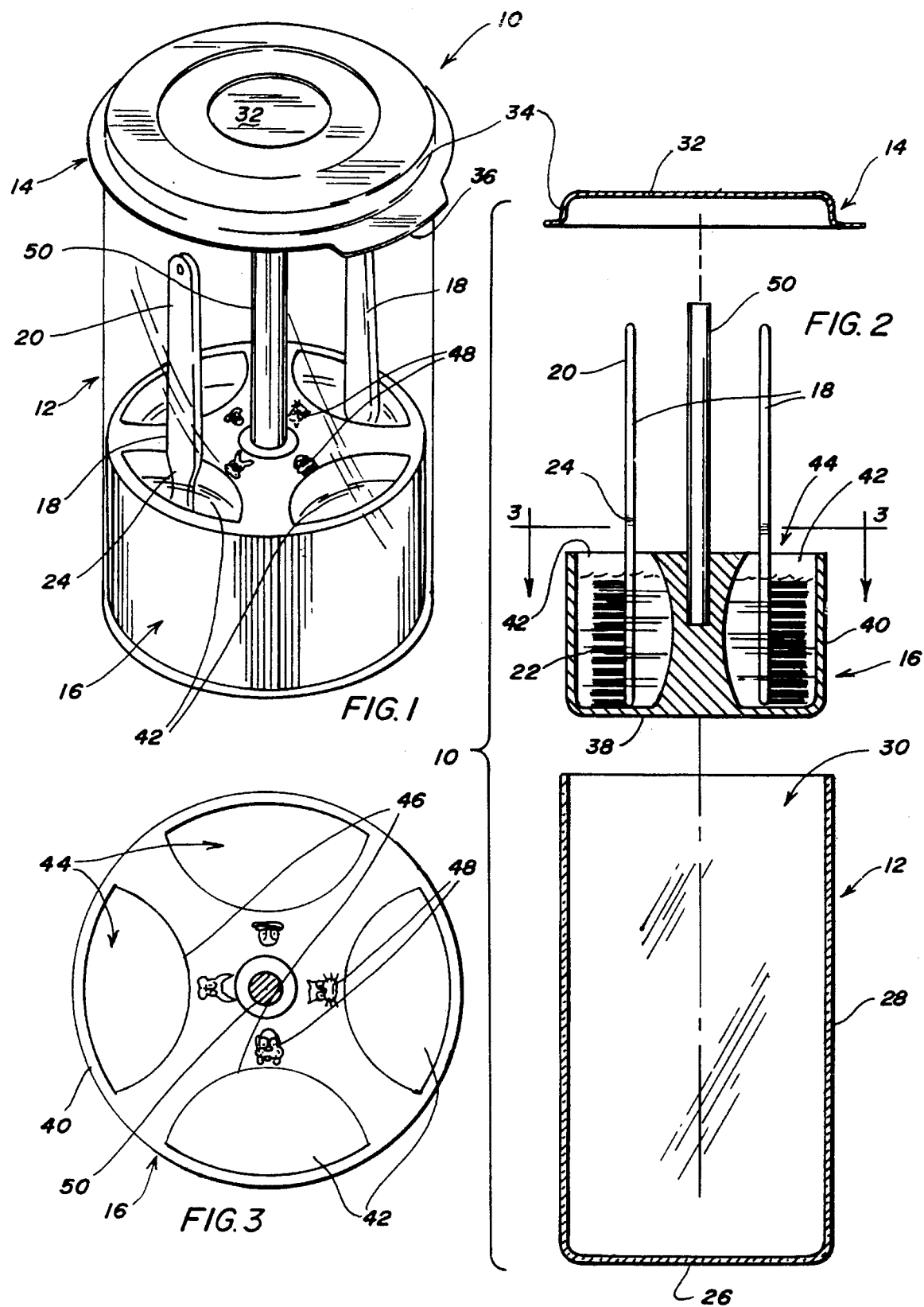

TOOTHBRUSH HOLDER

BACKGROUND OF THE INVENTION

1. Field of the Invention

The present invention relates to a sanitary holder for storing a plurality of toothbrushes between brushings.

2. Brief Description of the Prior Art

Ordinary toothbrush holders can be a vector in the spread of disease from one family member to another. It is well recognized that toothbrushes are a potential breeding ground for bacteria as not all contaminants are removed from a toothbrush by rinsing, providing a ready media for bacterial growth. Bathrooms are generally maintained at a higher temperature and humidity than the rest of the house, also contributing to the growth of germs.

Toothbrush holders such as racks, cups and the like hold a group of toothbrushes in close, frequently touching proximity. During periods of illness, exposed toothbrushes in a holder promotes, even guaranties, the possibility of germ transfer from family member to family member.

Various devices have been proposed for holding and sterilizing toothbrushes but they are generally complicated to use or to manufacture, which may account for the fact that none are in common use. Mandatory requirements include easy access to the toothbrushes and easy cleaning as a toothbrush holder otherwise will not be used for long. It is also important that the toothbrush holder be aesthetically pleasing, particularly if it is intended to sit on a counter in the bathroom.

SUMMARY OF THE INVENTION

In view of the above, it is an object of the present invention to provide a sanitary holder for storing a plurality of toothbrushes that provides easy access to the toothbrushes and is easy to clean. It is also an object to provide a holder that is easy to manufacture and aesthetically pleasing. Other objects and features of the invention will be in part apparent and in part pointed out hereinafter.

In accordance with the invention, a toothbrush holder has a container with a closed bottom, sidewall and an open top, with the open top and the bottom being spaced apart a distance greater than the length of a toothbrush having a handle and a bristle portion. The container is closed with a removable cap and a tray with a handle is slidable through the open top and between the sidewall of the container by the handle.

The tray has a bottom and a closed sidewall and is divided into a plurality of separate receptacles for holding a liquid antiseptic. Each receptacle has an open top and sidewall and is adapted to receive the bristle portion of the toothbrush immersed in the liquid antiseptic such that the bristles are immersed. The handle extends upwardly above the open receptacles and is adapted to be grasped by a user at the open end of the container. Sliding movement of the tray in the container is stopped when the bottom of the tray reaches the bottom of the container.

The invention summarized above comprises the constructions hereinafter described, the scope of the invention being indicated by the subjoined claims.

BRIEF DESCRIPTION OF THE DRAWINGS

In the accompanying drawings, in which one of various possible embodiments of the invention is illustrated, corresponding reference characters refer to corresponding parts throughout the several views of the drawings in which:

FIG. 1 is a perspective view of a toothbrush holder in accordance with the present invention;

FIG. 2 is an exploded view of the toothbrush holder in major part comprising a cap, tray and container; and, FIG. 3 is plan view of the tray, partly in section, taken along line 3—3 in FIG. 2.

DETAILED DESCRIPTION OF THE INVENTION

Referring to the drawings more particularly by reference number, reference numeral 10 refers to a toothbrush holder in accordance with the present invention, comprising in major part a container 12 with a removable cap 14 and a tray 16 which is stored in the container. Container 12 is designed for use in storing a plurality of toothbrushes 18, typically four or more but possibly less. Each toothbrush 18 has a handle portion 20 and a bristle portion 22 and is necked down at 24 adjacent the bristle portion.

Container 12 has a closed bottom 26, sidewall 28 and an open top 30 with the open top and the bottom spaced apart a distance greater than the length of the toothbrushes. In the form illustrated, container 12 has a cylindrical body with sidewall 28 being cylindrical and bottom 26 being circular. In a simple form, cap 14 has a top 32 and sidewall 34 and slip fits over the open end of container 12 with the inside of top 32 resting on the top edge of container sidewall 28. Cap sidewall 34 may be flanged with an ear 36 provided to facilitate removal of cap 14 from container 12. Cap 14 and container 12 may be cooperatively threaded or the like for more secure attachment.

Tray 16 has a bottom 38 and a sidewall 40 and is divided into a plurality of separate receptacles 42 for holding a liquid antiseptic, including within that general term disinfectants, germicides or the like. When container 12 has a cylindrical body, tray sidewall 40 is preferably cylindrical and bottom 38 circular. Each of receptacles 42 has an open top 44 and a closed sidewall 46 and is adapted to receive bristle portion 22 of toothbrush 18 such that the bristles are immersed in the antiseptic preferably along with handle portion 20 up to necked down portion 24. Indicia 48 such as animal figures (as shown), numbers, letters (including Braille) or the like may be used to mark the receptacles such that each user can be assigned a receptacle.

A handle 50 extends upwardly above open receptacles 42 and is attached to tray 16. As illustrated, four receptacles 42 are symmetrically arranged about tray 16 with sidewall 40 of tray 16 forming the outer sidewall 46 of receptacle 42 and with handle 50 being a rod attached to the middle of the tray. The width and shape of tray 16 is such that it is slidable through open top 30 and between sidewall 28 of container 12 by handle 50 until the bottom of tray is stopped by the bottom of the container. For this purpose handle 50 extends upwardly to within about ½ inch of the upper edge of container sidewall 28 such that it can be grasped by a user at the open end of the container without contacting the inside of container sidewall 28 and possibly contaminating them. Entirely satisfactory results have been obtained with a container for holding four toothbrushes having a cylindrical body about 3½" across and about 8" tall. In this instance, the tray measured 3" across and the tip of the handle was 7½" above the bottom of container 12.

Container 12, cap 14 and tray 16 can be molded of a plastic material or the like. Handle 50 can be formed with tray 16 or it can be formed separately of plastic, metal, etc.

and sonicly or solvent welded to tray 16, attached with a screw or the like appropriate to the material. It is preferred that sidewall 28 of container 12 be transparent to allow the user to easily pick a toothbrush, although this is not critical as when tray 16 is pulled out of container 12 by handle 50, the color is easily distinguished. For ease of manufacture, bottom 26 of container 12 can be made of the same material as sidewall 28 and be transparent. It is preferred that cap 14 be formed of opaque plastic material and be somewhat flexible such that it can be easily removed from container 12. Tray 16 may be molded of a plastic material that is resistant to degradation in continuous contact with antiseptic fluids and be transparent or opaque.

In use, cap 14 is removed and tray 16 withdrawn from container 12. Enough receptacles 42 are filled with antiseptic to accommodate the number of toothbrushes to be stored. Suitable liquids for this purpose include commercially available mouthwashes and other over-the-counter and prescription disinfectants and germicides. Using indicia 48, each toothbrush is assigned to a receptacle and immersed in the antiseptic. Tray 16 is then slid into container 12 by handle 50 and cap 14 attached to keep the antiseptic from evaporating and to keep air-carried germs from getting into the container.

When a person wants to brush his teeth with his toothbrush stored in container 12, he removes cap 14 and withdraws tray 16 by handle 50. He then removes his toothbrush from its assigned receptacle 42. After he is finished brushing, he then puts his toothbrush back into its receptacle, slides tray back into container and reattaches cap 14. While the above procedure is preferred, it is recognized that some family members will stick their hands into container 12 and pull out a toothbrush without removing tray 16. At selected intervals, all of the toothbrushes can be removed, receptacles drained and cap, container and tray washed. Receptacles are then refilled, toothbrushes reinstalled, tray slid back into container and cap attached, ready for use.

In view of the above, it will be seen that the several objects of the invention are achieved and other advantageous results attained. As various changes could be made in the above constructions without departing from the scope of the invention, it is intended that all matter contained in the above description or shown in the accompanying drawings shall be interpreted as illustrative and not in a limiting sense.

What is claimed:

1. A toothbrush holder comprising an unpartitioned container with a closed bottom, a sidewall and an open top, said open top and said bottom being spaced apart a distance greater than the length of a toothbrush having a handle and a bristle portion;

a removable cap for closing the open top of the container;

a tray with a bottom and a sidewall, said tray divided into a plurality of separate receptacles for holding a liquid antiseptic, each receptacle consisting of an open top and a closed bottom and a sidewall with a depth adapted to receive the bristle portion of the toothbrush such that substantially only the bristles are immersed in the liquid antiseptic;

said tray further having a handle attached to the tray, said handle extending upwardly above the open receptacles, said tray being slidable through the open top and between the sidewall of the container by said handle, said handle being adapted to be grasped by a user at the open end of the container and said tray being stopped when the bottom of the tray reaches the bottom of the container.

2. The toothbrush holder of claim 1 wherein the container and the tray are cylindrical bodies, the sidewall of each being cylindrical and the bottom of each being circular.

3. The toothbrush holder of claim 2 wherein the receptacles are symmetrically arranged about the tray and the handle is a rod attached to the middle of the tray.

4. The toothbrush holder of claim 1 wherein the tray has indicia for marking the receptacles.

5. A toothbrush holder comprising an unpartitioned container with a closed bottom, a transparent sidewall and an open top, said open top and said bottom being spaced apart a distance greater than the length of a toothbrush having a handle and a bristle portion;

a removable cap for closing the open top of the container;

a tray with a bottom and a sidewall, said tray divided into a plurality of separate receptacles for holding a liquid antiseptic, said receptacles resistant to constant contact with antiseptic liquids and marked with identifying indicia, each receptacle consisting of an open top and a closed bottom and a sidewall with a depth adapted to receive the bristle portion of the toothbrush such that substantially only the bristles are immersed in the liquid antiseptic;

said tray further having a handle attached to the tray, said handle extending upwardly above the open receptacles, said tray being slidable through the open top and between the sidewall of the container by said handle, said handle being adapted to be grasped by a user at the open end of the container and said tray being stopped when the bottom of the tray reaches the bottom of the container.

6. The toothbrush holder of claim 5 wherein the container and the tray are cylindrical bodies, the sidewall of each being cylindrical and the bottom of each being circular.

7. The toothbrush holder of claim 6 wherein the receptacles are symmetrically arranged about the tray and the handle is a rod attached to the middle of the tray.

8. The toothbrush holder of claim 7 wherein the container is about 3½ inches across and about 8 inches high and wherein the tray is about 3 inches across and the handle extends to within about ½ inch of the open top of the container.

\* \* \* \* \*